(12) United States Patent
Ozeki et al.

(10) Patent No.: US 11,320,134 B2
(45) Date of Patent: May 3, 2022

(54) COOLING DEVICE, LIGHT SOURCE DEVICE, AND MEDICAL OBSERVATION SYSTEM

(71) Applicants: Sony Corporation, Tokyo (JP); Sony Olympus Medical Solutions Inc., Tokyo (JP)

(72) Inventors: Motoki Ozeki, Aichi (JP); Yoichiro Sakanoue, Tokyo (JP)

(73) Assignees: SONY CORPORATION, Tokyo (JP); SONY OLYMPUS MEDICAL SOLUTIONS INC., Tokyo (JP)

( * ) Notice: Subject to any disclaimer, the term of this patent is extended or adjusted under 35 U.S.C. 154(b) by 204 days.

(21) Appl. No.: 16/741,747

(22) Filed: Jan. 14, 2020

(65) Prior Publication Data
US 2020/0300451 A1 Sep. 24, 2020

(30) Foreign Application Priority Data

Mar. 20, 2019 (JP) .............................. JP2019-053836

(51) Int. Cl.
| | |
|---|---|
| *F21V 29/76* | (2015.01) |
| *A61B 1/06* | (2006.01) |
| *F21V 29/67* | (2015.01) |
| *A61B 1/12* | (2006.01) |
| *A61B 1/00* | (2006.01) |
| *F21V 29/51* | (2015.01) |
| *F21W 131/20* | (2006.01) |

(52) U.S. Cl.
CPC ........ *F21V 29/763* (2015.01); *A61B 1/00197* (2013.01); *A61B 1/0661* (2013.01); *A61B 1/128* (2013.01); *F21V 29/51* (2015.01); *F21V 29/673* (2015.01); *F21V 29/767* (2015.01); *F21W 2131/20* (2013.01)

(58) Field of Classification Search
CPC .... F21V 29/673; F21V 29/763; F21V 29/767; F21V 29/00–90; A61B 1/06–07
See application file for complete search history.

(56) References Cited

U.S. PATENT DOCUMENTS

2017/0075201 A1\* 3/2017 Terasaki ................ F21V 29/673

FOREIGN PATENT DOCUMENTS

JP 6329708 B2 5/2018

\* cited by examiner

*Primary Examiner* — Sean P Gramling
(74) *Attorney, Agent, or Firm* — Xsensus LLP (57) ABSTRACT

A cooling device includes: a casing including an air intake port and an air exhaust port; a single heat releaser including a plurality of fins arranged in a gas flow path from the air intake port to the air exhaust port; a first heat diffuser arranged in the casing, connected to a first heat generation body generating heat at time of driving and the single heat releaser in a heat-transferable manner, and arranged at a position forming a part of the gas flow path passing through a space between the plurality of fins; and a second heat diffuser arranged in the casing, connected to a second heat generation body generating heat at time of driving and the single heat releaser in a heat-transferable manner, and arranged at a position forming a part of the gas flow path passing through the space between the plurality of fins.

20 Claims, 9 Drawing Sheets

COOLING DEVICE, LIGHT SOURCE DEVICE, AND MEDICAL OBSERVATION SYSTEM

This application claims priority from Japanese Application No. 2019-053836, filed on Mar. 20, 2019, the contents of which are incorporated by reference herein in its entirety.

BACKGROUND

The present disclosure relates to a cooling device cooling a heat source, a light source device, and a medical observation system.

In a medical observation system such as an endoscope, there is known a technique for using a plurality of solid state light emitting devices as a light source device for the endoscope (for example, refer to JP 6329708 B2). In this technique, to cool heat generation from the plurality of solid state light emitting devices, each solid state light emitting device is separately cooled by a cooling device providing the solid state light emitting device with a heat sink.

SUMMARY

However, in JP 6329708 B2 described above, since each solid state light emitting device is provided with the heat sink, an installation area for installing the respective heat sinks is required, which causes a problem in which the cooling device increases in size.

There is a need for a cooling device, a light source device, and a medical observation system enabling size reduction.

According to one aspect of the present disclosure, there is provided a cooling device including: a casing including an air intake port and an air exhaust port; a single heat releaser including a plurality of fins arranged in a gas flow path from the air intake port to the air exhaust port; a first heat diffuser arranged in the casing, connected to a first heat generation body generating heat at time of driving and the single heat releaser in a heat-transferable manner, and arranged at a position forming a part of the gas flow path passing through a space between the plurality of fins; and a second heat diffuser arranged in the casing, connected to a second heat generation body generating heat at time of driving and the single heat releaser in a heat-transferable manner, and arranged at a position forming a part of the gas flow path passing through the space between the plurality of fins.

DETAILED DESCRIPTION

Hereinbelow, modes for carrying out the present disclosure (hereinbelow referred to as "embodiments") will be described in detail with reference to the drawings. Note that the present disclosure is not limited by the following embodiments. Also, each figure referred to in the following description merely illustrates a shape, a size, and a positional relationship as schematically as the content of the present disclosure may be understood. That is, in the present disclosure, the shape, the size, and the positional relationship are not limited to those illustrated in each figure. Further, to illustrate figures, identical components are labeled with the same reference signs. Still further, as an example of a medical observation system according to the present disclosure, an endoscope system will be described.

First Embodiment

Configuration of Endoscope System

Figure 1:
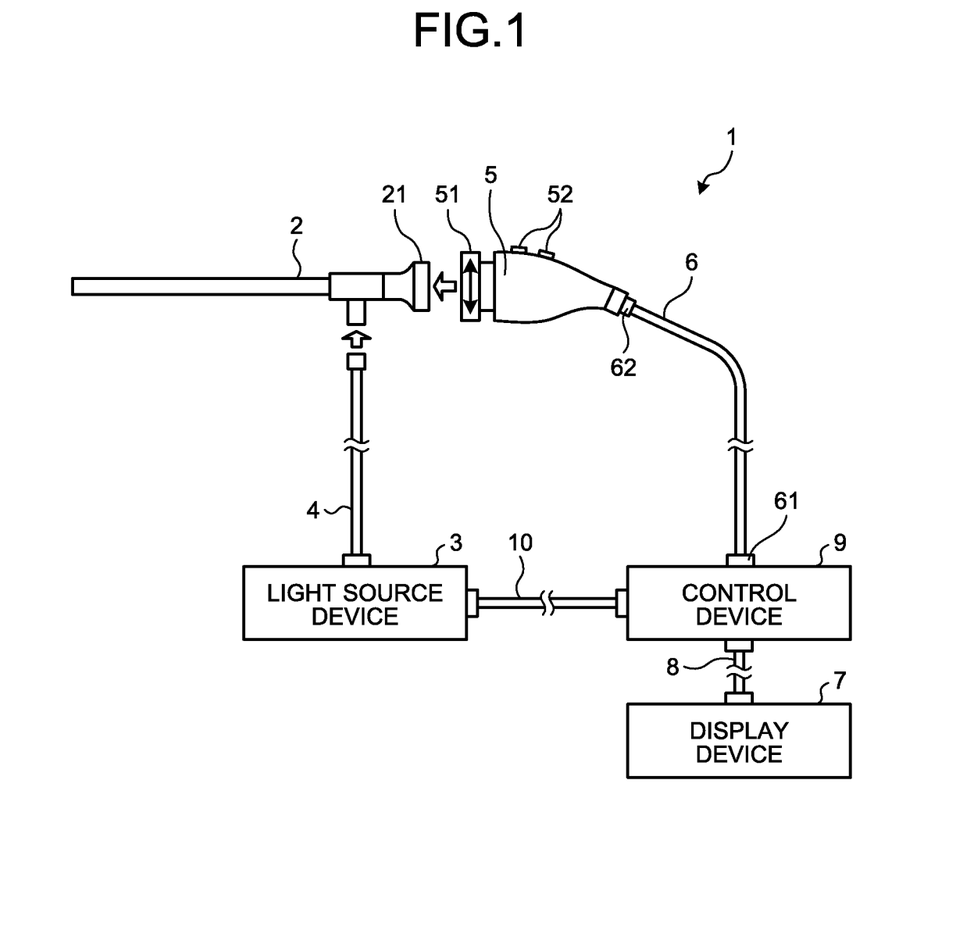
FIG. 1 illustrates a schematic configuration of an endoscope system according to a first embodiment.

FIG. 1 illustrates a schematic configuration of an endoscope system according to a first embodiment. An endoscope system 1 illustrated in FIG. 1 is a system used in a medical field, inserted into an inside of a subject such as a living body of a human being or an animal (into a living body), and displaying an image obtained by capturing an image of the inside to cause the subject to be observed. Note that, in the first embodiment, although a rigid endoscope system using a rigid endoscope (insertion unit 2) illustrated in FIG. 1 will be described as the endoscope system 1, the endoscope system 1 may be a flexible endoscope system, for example.

The endoscope system 1 illustrated in FIG. 1 includes the insertion unit 2 (rigid endoscope), a light source device 3, a light guide 4, a camera head 5 (imaging device for the endoscope), a first transmission cable 6, a display device 7, a second transmission cable 8, a control device 9, and a third transmission cable 10. Note that, in the first embodiment, the insertion unit 2, the light guide 4, the camera head 5, and the first transmission cable 6 function as an endoscope.

The insertion unit 2 is rigid or at least partially flexible, is formed in an elongated shape, and is inserted into the subject such as a patient. Inside the insertion unit 2 is provided an optical system including one or a plurality of lens(es) and forming an observation image.

To the light source device 3, one end of the light guide 4 is connected. The light source device 3 emits (supplies) white light or the like adapted to illuminate the inside of the subject to the one end of the light guide 4 under control of the control device 9. The light source device 3 includes a light emitting diode (LED) light source or a semiconductor laser element such as a laser diode (LD). The light source device 3 and the control device 9 may be configured to communicate separately as illustrated in FIG. 1 or may be configured integrally. Meanwhile, a detailed configuration of the light source device 3 will be described below.

The one end of the light guide 4 is removably connected to the light source device 3, and the other end thereof is removably connected to the insertion unit 2. The light guide 4 guides light emitted from the light source device 3 from the one end to the other end and supplies the light to the insertion unit 2.

To the camera head 5, an ocular unit 21 of the insertion unit 2 is removably connected. The camera head 5 captures an observation image formed by the insertion unit 2 to generate an imaging signal and outputs the imaging signal (electric signal) under control of the control device 9. Also, the camera head 5 includes an operation ring unit 51 provided to be rotatable in a circumferential direction and a plurality of input units 52 receiving input of an instruction signal instructing various operations of the endoscope system 1.

One end of the first transmission cable 6 is removably connected to the control device 9 via a first connector unit 61, and the other end thereof is connected to the camera head 5 via a second connector unit 62. The first transmission cable 6 transmits an imaging signal output from the camera head 5 to the control device 9 and transmits a control signal, a synchronization signal, a clock signal, electric power, and the like output from the control device 9 to the camera head 5.

The display device 7 may be connected to the control device 9 via the second transmission cable 8 and displays a display image based on an image signal processed in the control device 9 or various kinds of information regarding the endoscope system 1 under control of the control device 9.

One end of the second transmission cable 8 is removably connected to the display device 7, and the other end thereof is removably connected to the control device 9. The second transmission cable 8 transmits to the display device 7 the display image based on the image signal processed in the control device 9.

The control device 9 includes a memory and a processor including hardware such as a central processing unit (CPU), a graphics processing unit (GPU), an application specific integrated circuit (ASIC), and a field programmable gate array (FPGA) and comprehensively controls operations of the light source device 3, the camera head 5, and the display device 7 via the first transmission cable 6, the second transmission cable 8, and the third transmission cable 10 in accordance with a program recorded in the memory.

One end of the third transmission cable 10 is removably connected to the light source device 3, and the other end thereof is removably connected to the control device 9. The third transmission cable 10 transmits a control signal from the control device 9 to the light source device 3.

Detailed Configuration of Light Source Device

Next, a detailed configuration of the light source device 3 will be described.

Figure 2:
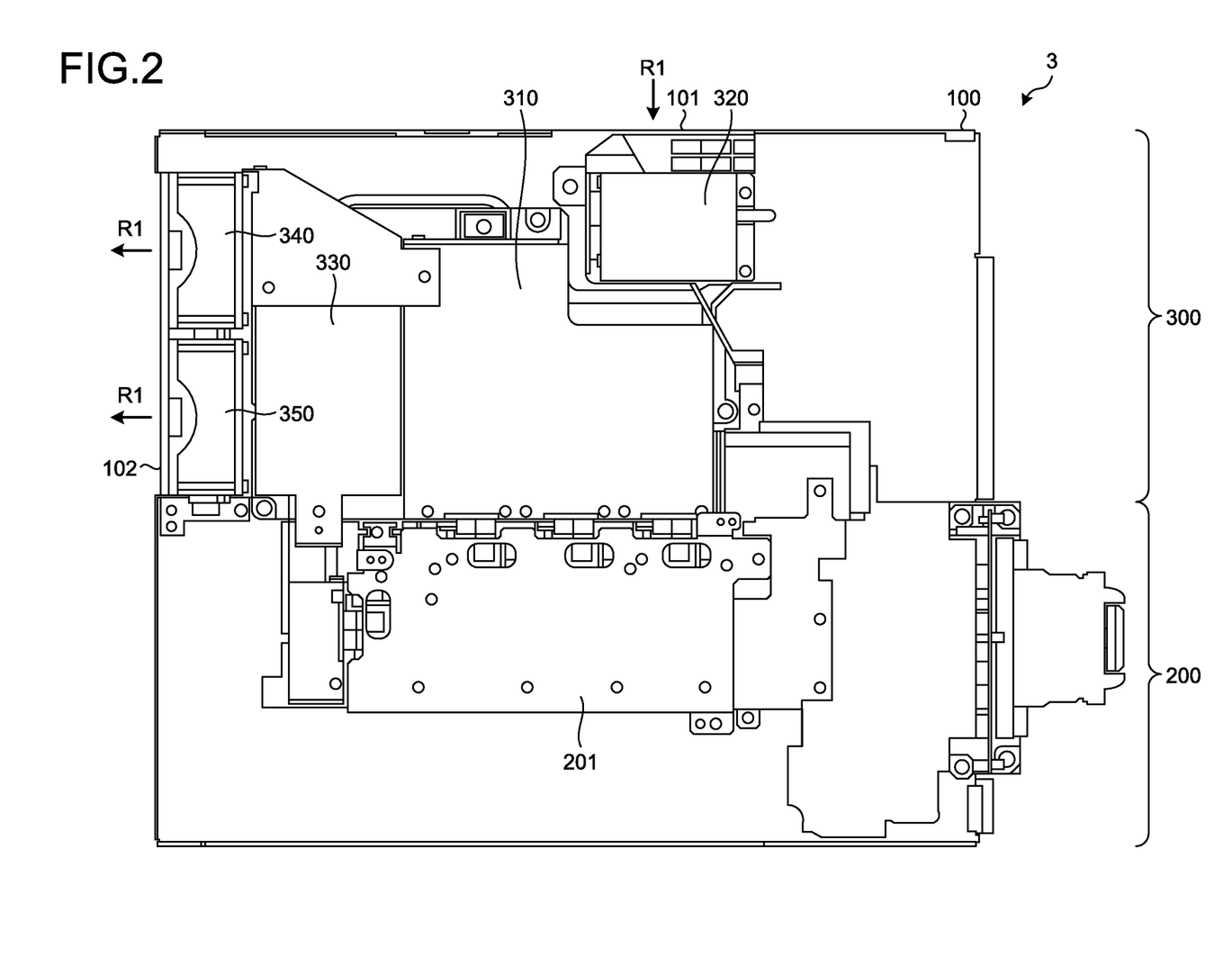
FIG. 2 is an upper view illustrating a schematic configuration of an inside of a light source device according to the first embodiment.

FIG. 2 is an upper view illustrating a schematic configuration of an inside of the light source device 3.

Figure 3:
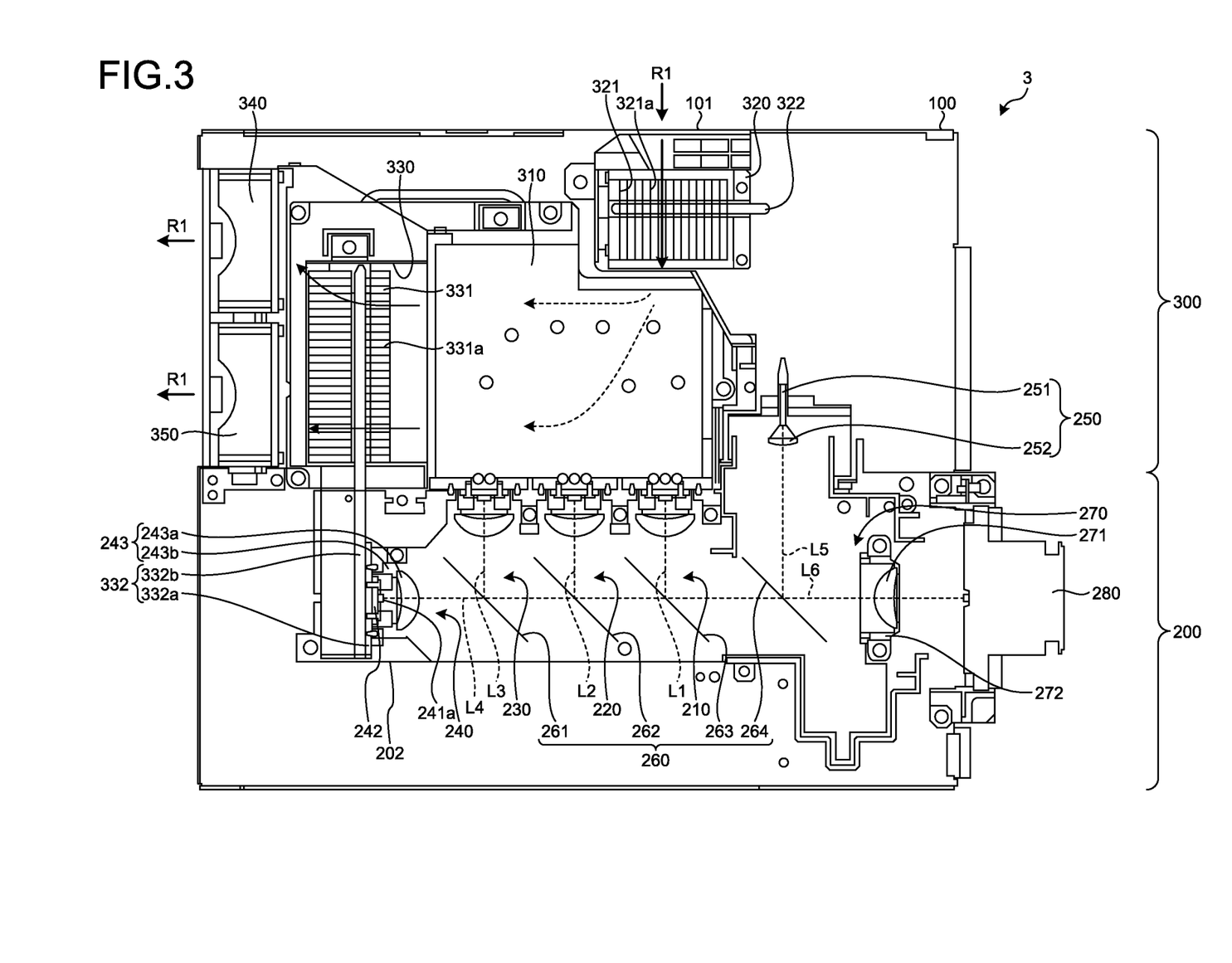
FIG. 3 is an upper view illustrating a schematic configuration of the light source device according to the first embodiment in a state in which lid portions of respective units of the light source device are removed.

FIG. 3 is an upper view illustrating a schematic configuration of the light source device 3 in a state in which lid portions of respective units of the light source device 3 are removed.

As illustrated in FIGS. 2 and 3, the light source device 3 includes a casing 100, an illumination light emitting unit 200, and a cooling device 300.

Configuration of Casing

First, a configuration of the casing 100 will be described.

As illustrated in FIGS. 2 and 3, the casing 100 houses the illumination light emitting unit 200 and the cooling device 300. The casing 100 includes an air intake port 101 taking air R1 from an outside and an air exhaust port 102 exhausting the air R1 inside the casing 100 to the outside.

Configuration of Illumination Light Emitting Unit

Next, a configuration of the illumination light emitting unit 200 will be described.

As illustrated in FIGS. 2 and 3, the illumination light emitting unit 200 includes an enclosure 201, a first light source unit 210, a second light source unit 220, a third light source unit 230, a fourth light source unit 240, a fifth light source unit 250, a light multiplexer 260, a light condenser 270, and a light emitter 280.

As illustrated in FIGS. 2 and 3, the enclosure 201 is arranged to enclose a below-mentioned optical member group in the casing 100 and is formed to approximately seal the optical member group by means of a first heat diffuser 313 and a second heat diffuser 314 of a first cooling unit 310 in the below-mentioned cooling device 300. Specifically, the enclosure 201 is formed to approximately seal the internal space by means of the first cooling unit 310, the casing 100, a sidewall 202, and the like. Also, the enclosure 201 encloses in the internal space the first light source unit 210, the second light source unit 220, the third light source unit 230, the fourth light source unit 240, the fifth light source unit 250, the light multiplexer 260, and the light condenser 270.

Figure 4:
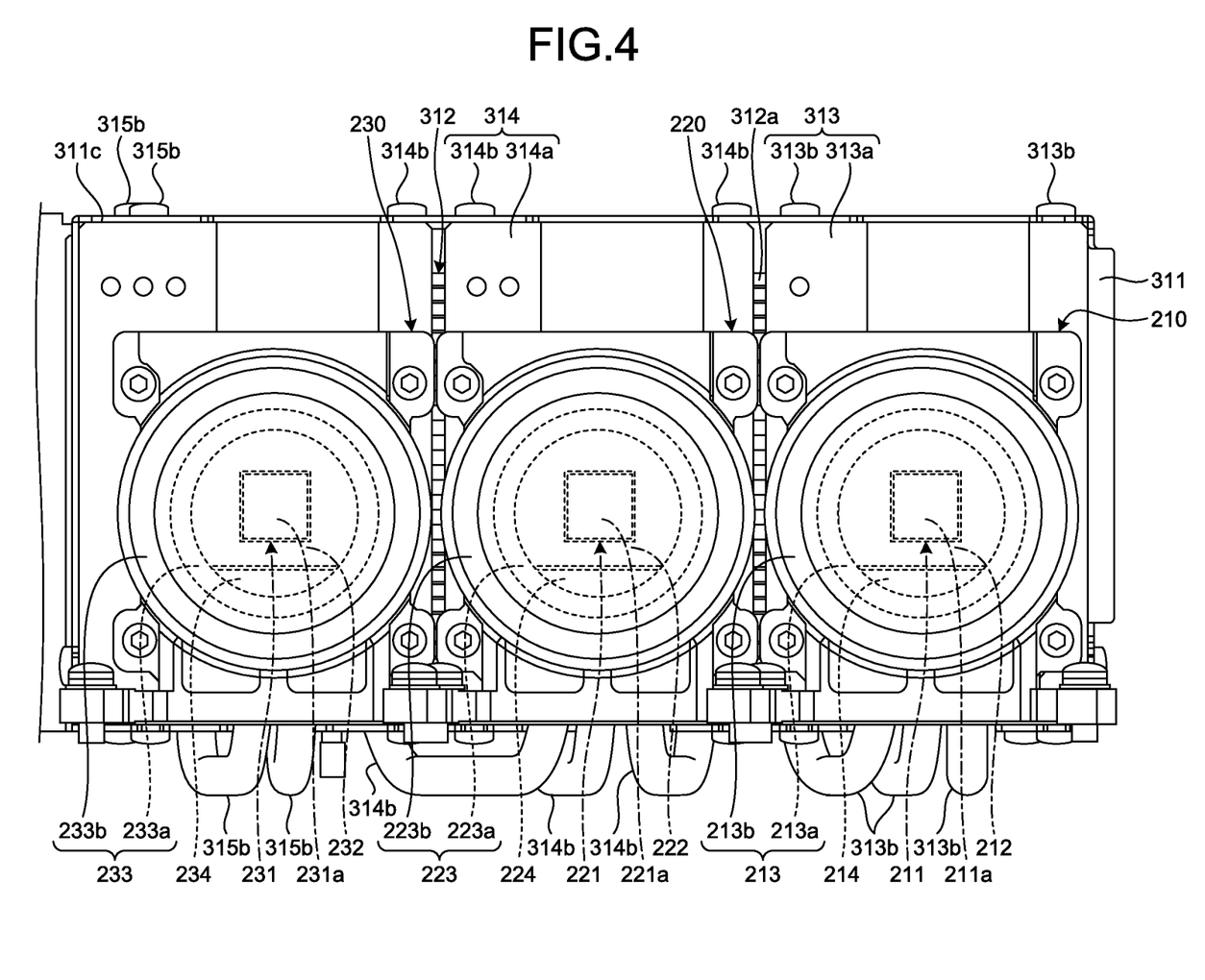
FIG. 4 illustrates schematic configurations of a first light source unit, a second light source unit, and a third light source unit according to the first embodiment.
Figure 5:
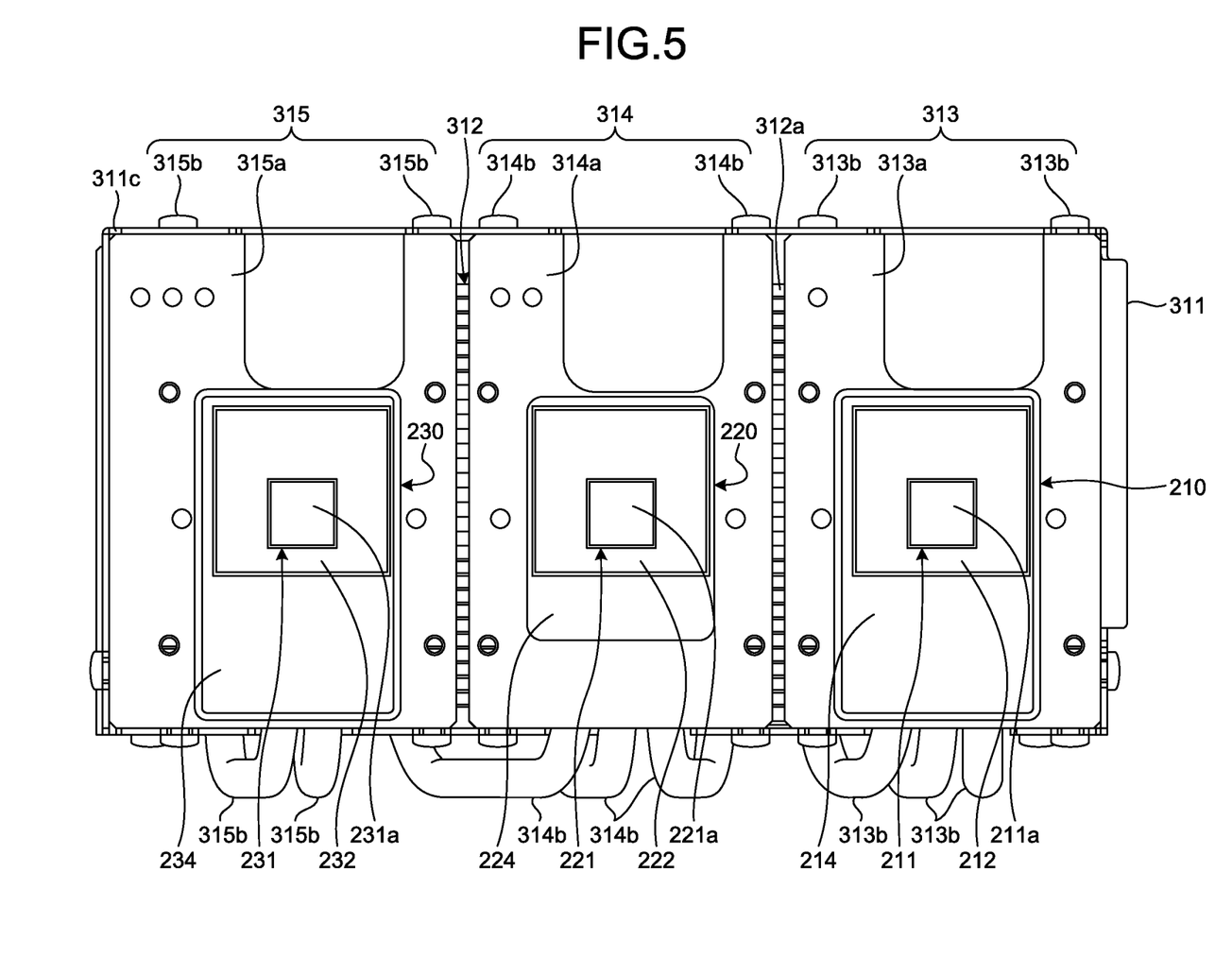
FIG. 5 is a front view illustrating schematic configurations of the first light source unit, the second light source unit, and the third light source unit according to the first embodiment from each of which an optical system is removed.

FIG. 4 illustrates schematic configurations of the first light source unit 210, the second light source unit 220, and the third light source unit 230. FIG. 5 is a front view illustrating schematic configurations of the first light source unit 210, the second light source unit 220, and the third light source unit 230 from each of which an optical system is removed.

As illustrated in FIGS. 2 to 5, the first light source unit 210 emits light having a red wavelength band (wavelength band: 600 nm to 700 nm), which is light having a second wavelength band (hereinbelow referred to as "R light"). The first light source unit 210 includes a first solid state light emitting device 211, a first circuit board 212, and a first optical system 213.

The first solid state light emitting device 211 is formed with use of a light emitting diode (LED) chip emitting R light and is implemented on the first circuit board 212. The first solid state light emitting device 211 has a rectangular sheet-like light emitting region 211*a* and emits R light from the sheet-like light emitting region 211*a* toward the front (the face on the lower side in FIG. 3) side. Note that, in the first embodiment, the first solid state light emitting device 211 functions as a first heat generation body.

The first circuit board 212 is arranged at a rear surface (a surface on the opposite side of the implemented surface of the first solid state light emitting device 211) side thereof via a first insulating unit 214 on a side surface of a frame unit 311 of the cooling device 300 perpendicular to a mounting surface on which the casing 100 is mounted, that is, on a below-mentioned first heat spreader 313*a* of the first heat diffuser 313.

The first optical system 213 condenses and collimates the R light emitted by the first solid state light emitting device 211 to emit the R light to the light multiplexer 260. The first optical system 213 is arranged on an optical axis L1 of the R light emitted by the first solid state light emitting device 211. The first optical system 213 includes a plurality of lenses 213a and a first lens frame 213b holding the plurality of lenses 213a.

The second light source unit 220 emits light having a green wavelength band (wavelength band: 500 nm to 600 nm), which is light having a first wavelength band (hereinbelow referred to as "G light"). The second light source unit 220 includes a second solid state light emitting device 221, a second circuit board 222, and a second optical system 223.

The second solid state light emitting device 221 is formed with use of an LED chip emitting G light and is implemented on the second circuit board 222. The second solid state light emitting device 221 has a rectangular sheet-like light emitting region 221a and emits G light from the sheet-like light emitting region 221a toward the front side. Note that, in the first embodiment, the second solid state light emitting device 221 functions as a second heat generation body.

The second circuit board 222 is arranged at a rear surface (a surface on the opposite side of the implemented surface of the second solid state light emitting device 221) side thereof via a second insulating unit 224 on a side surface of the frame unit 311 of the cooling device 300 perpendicular to the mounting surface on which the casing 100 is mounted, that is, on a second heat spreader 314a of the below-mentioned second heat diffuser 314.

The second optical system 223 condenses and collimates the G light emitted by the second solid state light emitting device 221 to emit the G light to the light multiplexer 260. The second optical system 223 is arranged on an optical axis L2 of the G light emitted by the second solid state light emitting device 221. The second optical system 223 includes a plurality of lenses 222a and a second lens frame 222b holding the plurality of lenses 222a.

The third light source unit 230 emits light having a blue wavelength band (wavelength band: 400 nm to 500 nm) (hereinbelow referred to as "B light"). The third light source unit 230 includes a third solid state light emitting device 231, a third circuit board 232, and a third optical system 233.

The third solid state light emitting device 231 is formed with use of an LED chip emitting B light and is implemented on the third circuit board 232. The third solid state light emitting device 231 has a rectangular sheet-like light emitting region 231a and emits B light from the sheet-like light emitting region 231a toward the front side.

The third circuit board 232 is arranged at a rear surface (a surface on the opposite side of the implemented surface of the third solid state light emitting device 231) side thereof via a third insulating unit 234 on a side surface of the frame unit 311 of the cooling device 300 perpendicular to the mounting surface on which the casing 100 is mounted, that is, on a third heat spreader 315a of a below-mentioned third heat diffuser 315.

The third optical system 233 condenses the B light emitted by the third solid state light emitting device 231 to emit the B light to the light multiplexer 260. The third optical system 233 is arranged on an optical axis L3 of the B light emitted by the third solid state light emitting device 231. The third optical system 233 includes a plurality of lenses 232a and a third lens frame 232b holding the plurality of lenses 232a.

The fourth light source unit 240 emits light having a violet wavelength band (wavelength band: 380 nm to 450 nm) (hereinbelow referred to as "V light"). The fourth light source unit 240 includes a fourth solid state light emitting device 241, a fourth circuit board 242, and a fourth optical system 243.

The fourth solid state light emitting device 241 is formed with use of an LED chip emitting V light and is implemented on the fourth circuit board 242. The fourth solid state light emitting device 241 has a rectangular sheet-like light emitting region 241a and emits V light from the sheet-like light emitting region 241a toward the side surface (the face on the right side in FIG. 3).

The fourth circuit board 242 is arranged at a rear surface (a surface on the opposite side of the implemented surface of the fourth solid state light emitting device 241) side thereof via an insulating unit (not illustrated) on a below-mentioned fifth heat spreader 332a of a fifth heat diffuser 332 of a third cooling unit 330.

The fourth optical system 243 condenses and collimates the V light emitted by the fourth solid state light emitting device 241 to emit the V light to the light multiplexer 260. The fourth optical system 243 is arranged on an optical axis L4 of the V light emitted by the fourth solid state light emitting device 241. The fourth optical system 243 includes a plurality of lenses 242a and a fourth lens frame 242b holding the plurality of lenses 242a.

The fifth light source unit 250 emits light having a white wavelength band (hereinbelow referred to as "W light"). The fifth light source unit 250 includes a fifth emitting unit 251 and a fifth optical system 252.

The fifth emitting unit 251 is formed with use of a laser diode (LD) emitting W light, a fiber, a lens, and the like and emits W light toward the front side.

The fifth optical system 252 condenses the W light emitted by the fifth emitting unit 251 to emit the W light to the light multiplexer 260. The fifth optical system 252 is arranged on an optical axis L5 of the W light emitted by the fifth emitting unit 251. The fifth optical system 252 is formed with use of a plurality of lenses.

The light multiplexer 260 compounds light emitted by the first light source unit 210, the second light source unit 220, the third light source unit 230, the fourth light source unit 240, and the fifth light source unit 250 and emits the light to the light condenser 270. The light multiplexer 260 includes a first dichroic mirror 261, a second dichroic mirror 262, a third dichroic mirror 263, and a fourth dichroic mirror 264. Note that, in the first embodiment, the first optical system 213, the second optical system 223, the third optical system 233, the fourth optical system 243, the fifth optical system 252, the light multiplexer 260, and the light condenser 270 function as the optical member group compounding the R light, the G light, the B light, the V light, and the W light and guiding the light to the light emitter 280. Also, the respective reflection surfaces of the first dichroic mirror 261, the second dichroic mirror 262, the third dichroic mirror 263, and the fourth dichroic mirror 264 are inclined approximately at 45 degrees to an optical axis L6 of the light condenser 270 and are arranged in the enclosure 201.

The first dichroic mirror 261 reflects the B light emitted by the third light source unit 230 toward the second dichroic mirror 262 and transmits the V light emitted by the fourth light source unit 240 toward the second dichroic mirror 262.

The second dichroic mirror 262 reflects the G light emitted by the second light source unit 220 toward the third dichroic mirror 263 and transmits the light coming from the first dichroic mirror 261 toward the third dichroic mirror 263.

The third dichroic mirror 263 reflects the R light emitted by the first light source unit 210 toward the fourth dichroic mirror 264 and transmits the light coming from the second dichroic mirror 262 toward the fourth dichroic mirror.

The fourth dichroic mirror 264 reflects the W light emitted by the fifth light source unit 250 toward the light condenser 270 and transmits the light coming from the third dichroic mirror 263 toward the light condenser 270.

The light condenser 270 compounds the light coming from the light multiplexer 260 and condenses the light toward the light emitter 280. The light condenser 270 includes a plurality of lenses 271 and a lens holding frame 272 holding the plurality of lenses 271.

The light emitter 280 is optically connectable to the light guide 4 and emits the light condensed by the light condenser 270 toward the light guide 4.

Configuration of Cooling Device

Next, a configuration of the cooling device 300 will be described.

The cooling device 300 is a device cooling heat generated at the time of driving of the illumination light emitting unit 200. The cooling device 300 includes the first cooling unit 310, a second cooling unit 320, a third cooling unit 330, a first cooling fan 340, and a second cooling fan 350. In the cooling device 300, the second cooling unit 320, the first cooling unit 310, the third cooling unit 330, the first cooling fan 340, and the second cooling fan 350 are arranged in the casing 100 from the air intake port 101 to the air exhaust port 102 of the casing 100 in this order.

First, a configuration of the first cooling unit 310 will be described.

Figure 6:
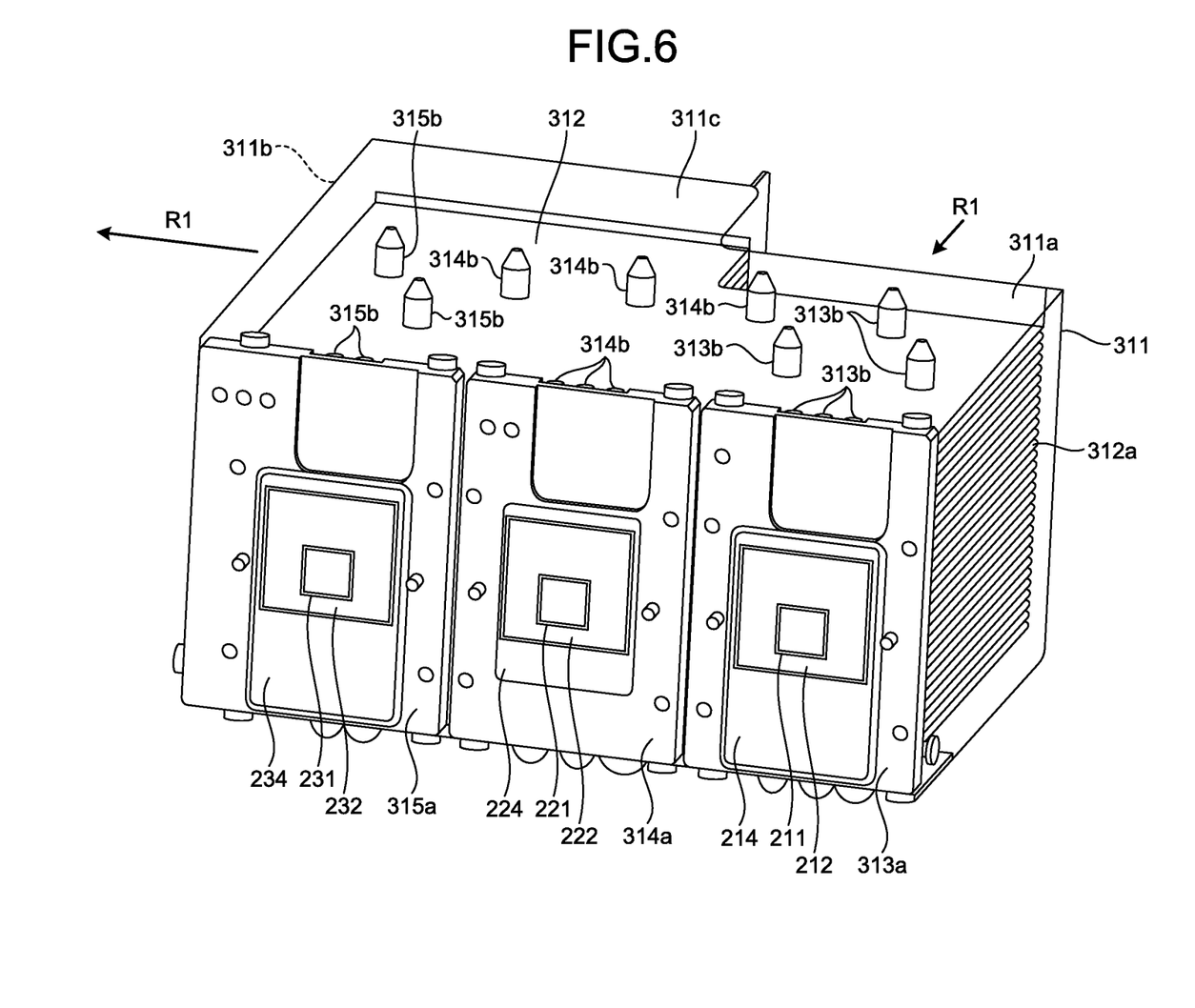
FIG. 6 is a perspective view illustrating a schematic configuration of a first cooling unit according to the first embodiment.
Figure 7:
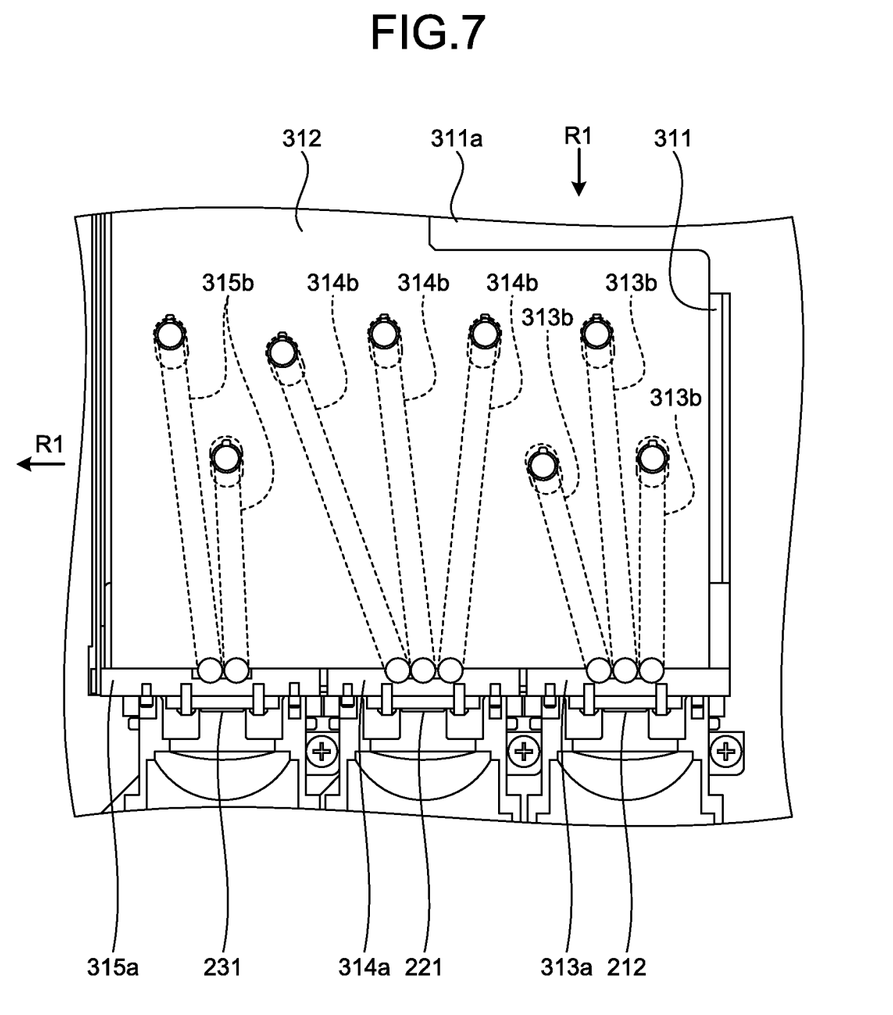
FIG. 7 is an enlarged view in which the upper surface of the first cooling unit according to the first embodiment is enlarged.

FIG. 6 is a perspective view illustrating a schematic configuration of the first cooling unit 310. FIG. 7 is an enlarged view in which the upper surface of the first cooling unit 310 is enlarged.

As illustrated in FIGS. 5 to 7, the first cooling unit 310 separately cools heat generated at each time of driving of each of the first light source unit 210, the second light source unit 220, and the third light source unit 230. The first cooling unit 310 includes a frame unit 311, a first heat releaser 312, the first heat diffuser 313, the second heat diffuser 314, and the third heat diffuser 315.

The frame unit 311 is provided on a flow path from the air intake port 101 to the air exhaust port 102 and houses the first heat releaser 312 therein. The frame unit 311 is formed in a rectangular shape and houses a plurality of below-mentioned fins 312a of the single first heat releaser 312. The frame unit 311 regulates arrangement of the plurality of fins 312a. Specifically, the frame unit 311 arranges the plurality of fins 312a so that the fins 312a may be parallel to the mounting surface on which the casing 100 is mounted. The plurality of fins 312a are arranged at predetermined spaces.

The first heat releaser 312 is provided on the flow path from the air intake port 101 to the air exhaust port 102. The first heat releaser 312 is formed with use of a heat sink. Specifically, the first heat releaser 312 includes the plurality of fins 312a. Each of the plurality of fins 312a is formed approximately in a flat plate shape made of a highly heat-conductive material. The plurality of fins 312a are laminated in a direction perpendicular to the mounting surface on which the frame unit 311 is mounted to mutually have predetermined spaces. Also, in the first heat releaser 312, the first heat diffuser 313, the second heat diffuser 314, and the third heat diffuser 315 are arranged on a side surface in a depth direction opposed to the air intake port 311a to form a part of the flow path of the air R1 flowing through the space between the plurality of fins 312a.

One end of the first heat diffuser 313 is connected to be heat-transferable to the first solid state light emitting device 211, and the other end thereof penetrates the plurality of fins 312a of the first heat releaser 312 and is connected to be heat-transferable to the plurality of respective fins 312a. The first heat diffuser 313 is arranged at a position forming a part of the flow path of gas passing between the plurality of fins 312a. The first heat diffuser 313 includes a first heat spreader 313a and a first plurality of heat pipes 313b.

The first heat spreader 313a is formed in a flat plate shape and is arranged on a side surface of the frame unit 311 in the depth direction opposed to the air intake port 311a of the frame unit 311. The first heat spreader 313a is connected to be heat-transferable via the first insulating unit 214 to the rear surface of the first circuit board 212 on which the first solid state light emitting device 211 is implemented.

One end of each of the first plurality of heat pipes 313b is connected to be heat-transferable to the first heat spreader 313a, and the other end thereof penetrates the plurality of fins 312a of the first heat releaser 312 and is connected to be heat-transferable to the plurality of respective fins 312a. Also, at least one of the first plurality of heat pipes 313b penetrates and is connected to be heat-transferable to the plurality of fins 312a so as to be arranged close to the air intake port 101.

One end of the second heat diffuser 314 is connected to be heat-transferable to the second solid state light emitting device 221, and the other end thereof penetrates the plurality of fins 312a of the first heat releaser 312 and is connected to be heat-transferable to the plurality of respective fins 312a. The second heat diffuser 314 is arranged at a position forming a part of the flow path of gas passing between the plurality of fins 312a. The second heat diffuser 314 includes a second heat spreader 314a and a second plurality of heat pipes 314b.

The second heat spreader 314a is formed in a flat plate shape and is arranged on the side surface of the frame unit 311 in the depth direction opposed to the air intake port 311a of the frame unit 311. The second heat spreader 314a is connected to be heat-transferable via the second insulating unit 224 to the rear surface of the second circuit board 222 on which the second solid state light emitting device 221 is implemented.

One end of each of the second plurality of heat pipes 314b is connected to be heat-transferable to the second heat spreader 314a, and the other end thereof penetrates the plurality of fins 312a of the first heat releaser 312 and is connected to be heat-transferable to the plurality of respective fins 312a. Also, the second plurality of heat pipes 314b penetrate and are connected to be heat-transferable to the plurality of fins 312a so as to be arranged close to the air intake port 101.

One end of the third heat diffuser 315 is connected to be heat-transferable to the third solid state light emitting device 231, and the other end thereof penetrates the plurality of fins 312a of the first heat releaser 312 and is connected to be heat-transferable to the plurality of respective fins 312a. The third heat diffuser 315 is arranged at a position forming a part of the flow path of gas passing between the plurality of fins 312a. The third heat diffuser 315 includes a third heat spreader 315a and a third plurality of heat pipes 315b.

The third heat spreader 315a is formed in a flat plate shape and is arranged on the side surface of the frame unit 311 in the depth direction opposed to the air intake port 311a of the frame unit 311. The third heat spreader 315a is connected to be heat-transferable via the third insulating unit 234 to the rear surface of the third circuit board 232 on which the third solid state light emitting device 231 is implemented.

One end of each of the third plurality of heat pipes 315b is connected to be heat-transferable to the third heat spreader 315a, and the other end thereof penetrates the plurality of fins 312a of the first heat releaser 312 and is connected to be heat-transferable to the plurality of respective fins 312a. Also, the third plurality of heat pipes 315b penetrate and are connected to be heat-transferable to the plurality of fins 312a so as to be arranged close to the air exhaust port 102.

In the first cooling unit 310 configured as above, heat generated at each of the first light source unit 210, the second light source unit 220, and the third light source unit 230 diffuses to the first heat spreader 313a, the second heat spreader 314a, and the third heat spreader 315a. Heat having diffused to the first heat spreader 313a, the second heat spreader 314a, and the third heat spreader 315a is transferred from the one ends to the other ends of the first plurality of heat pipes 313b, the second plurality of heat pipes 314b, and the third plurality of heat pipes 315b and is transferred to the plurality of fins 312a of the first heat releaser 312. Due to heat exchange between the plurality of fins 312a and air, heat is released from the plurality of fins 312a. Accordingly, with use of the first cooling unit 310, since only the single first heat releaser 312 may separately cool the first light source unit 210, the second light source unit 220, and the third light source unit 230, the size of the cooling device 300 may be reduced. Further, since the first heat spreader 313a, the second heat spreader 314a, and the third heat spreader 315a are separately connected via the first insulating unit 214, the second insulating unit 224, and the third insulating unit 234 to the first solid state light emitting device 211, the second solid state light emitting device 221, and the third solid state light emitting device 231, respectively, it is possible to prevent the first heat spreader 313a, the second heat spreader 314a, and the third heat spreader 315a from having the same potential.

Next, the second cooling unit 320 will be described.

The second cooling unit 320 cools heat generated at time of driving of the fifth light source unit 250. The second cooling unit 320 is arranged close to the air intake port 101 of the casing 100. The second cooling unit 320 includes a second heat releaser 321 and a fourth heat diffuser 322.

The second heat releaser 321 includes a plurality of fins 321a. Each of the plurality of fins 321a is formed approximately in a flat plate shape made of a highly heat-conductive material. The plurality of fins 321a are arranged perpendicularly to the mounting surface on which the casing 100 is mounted and are arranged to mutually have predetermined spaces.

One end of the fourth heat diffuser 322 is connected to be heat-transferable to the fifth light source unit 250, and the other end thereof penetrates the plurality of fins 321a of the second heat releaser 321 and is connected to be heat-transferable to the plurality of respective fins 321a. The fourth heat diffuser 322 is formed with use of a heat pipe.

Accordingly, heat generated at the fifth light source unit 250 diffuses to a heat spreader (not illustrated). Also, heat having diffused to the heat spreader is transferred from the one end to the other end of the fourth heat diffuser 322 and is transferred to the plurality of fins 321a of the second heat releaser 321. Due to heat exchange between the plurality of fins 321a and air, heat is released from the plurality of fins 321a.

Next, the third cooling unit 330 will be described.

The third cooling unit 330 cools heat generated at time of driving of the fourth light source unit 240. The third cooling unit 330 is arranged between the first cooling unit 310, and the first cooling fan 340 and the second cooling fan 350. The third cooling unit 330 includes a third heat releaser 331 and a fifth heat diffuser 332.

The third heat releaser 331 includes a plurality of fins 331a. Each of the plurality of fins 331a is formed approximately in a flat plate shape made of a highly heat-conductive material. The plurality of fins 331a are arranged perpendicularly to the mounting surface on which the casing 100 is mounted and are arranged to mutually have predetermined spaces.

One end of the fifth heat diffuser 332 is connected to be heat-transferable to the fourth light source unit 240, and the other end thereof penetrates the plurality of fins 331a of the third heat releaser 331 and is connected to be heat-transferable to the plurality of respective fins 331a. The fifth heat diffuser 332 includes a fifth heat spreader 332a and a fifth heat pipe 332b.

The fifth heat spreader 332a is formed in a flat plate shape. The fifth heat spreader 332a is connected to be heat-transferable via an insulating unit (not illustrated) to the rear surface of the fourth circuit board 242 on which the fourth solid state light emitting device 241 is implemented.

One end of the fifth heat pipe 332b is connected to be heat-transferable to the fifth heat spreader 332a, and the other end thereof penetrates the plurality of fins 331a of the third heat releaser 331 and is connected to be heat-transferable to the plurality of respective fins 331a.

Accordingly, heat generated at the fourth light source unit 240 diffuses via the fourth circuit board 242 to the fifth heat spreader 332a. Also, heat having diffused to the fifth heat spreader 332a is transferred from the one end to the other end of the fifth heat pipe 332b and is transferred to the plurality of fins 331a of the third heat releaser 331. Due to heat exchange between the plurality of fins 331a and air, heat is released from the plurality of fins 331a.

The first cooling fan 340 and the second cooling fan 350 are driven at predetermined rotation speed under control of the control device 9 to circulate a cooling medium (air) at a predetermined flow rate from the air intake port 101 to the air exhaust port 102 of the casing 100. Arrangement of the first cooling fan 340 and the second cooling fan 350 may arbitrarily be changed. For example, one of the first cooling fan 340 and the second cooling fan 350 may be arranged close to the air intake port 101. Also, in the first embodiment, another cooling fan may be provided in addition to the first cooling fan 340 and the second cooling fan 350.

According to the first embodiment described above, since the first heat diffuser 313 and the second heat diffuser 314 are connected to be heat-transferable to the single first heat releaser 312, and each of the first heat diffuser 313 and the second heat diffuser 314 is arranged at a position forming a part of the flow path, the size of the device may be reduced.

Also, according to the first embodiment, since the first heat diffuser 313 and the second heat diffuser 314 are connected to the frame unit 311 housing the plurality of fins 312a of the first heat releaser 312, the size of the device may be reduced.

Also, according to the first embodiment, since the first heat diffuser 313 and the second heat diffuser 314 are arranged to be away from each other on the frame unit 311, it is possible to prevent the first heat diffuser 313 and the second heat diffuser 314 from transferring heat to each other and to prevent the first heat diffuser 313 and the second heat diffuser 314 from having the same potential.

Also, according to the first embodiment, since the first heat diffuser 313 and the second heat diffuser 314 are arranged at positions opposed to the air intake port 311a of the frame unit 311, heat may be cooled efficiently.

Also, according to the first embodiment, since the second heat spreader 314a is arranged on the side surface of the frame unit 311 perpendicular to the mounting surface on which the casing 100 is mounted, which is the same as the side surface on which the first heat spreader 313a is arranged, and is formed as a part of the flow path through which air flows, heat may be cooled efficiently.

Also, according to the first embodiment, since the enclosure 201 is arranged to enclose the optical member group in the casing 100 and is formed to approximately seal the optical member group by means of the first heat diffuser 313 and the second heat diffuser 314, it is possible to prevent foreign matters and the like from entering the optical member group.

Also, according to the first embodiment, since the first solid state light emitting device 211 and the second solid state light emitting device 221 are provided with the first lens frame 213b holding the lenses 213a and the second lens frame 223b holding the lenses 223a, respectively, the optical axis may be adjusted easily.

Also, according to the first embodiment, the second solid state light emitting device 221, which emits light by itself in accordance with an observation mode, is arranged at the center on the side surface of the first heat releaser 312. Thus, in a case in which the second solid state light emitting device 221 emits light, heat of the second heat spreader 314a may be transferred to the first heat releaser 312 efficiently, and the cooling efficiency may thus be improved.

Also, in the first embodiment, although the areas of the first heat spreader 313a, the second heat spreader 314a, and the third heat spreader 315a are equal, the area ratio may be changed in accordance with the heat generation amounts of the respective solid state light emitting devices. For example, in a case in which the relationship among the heat generation amounts of the respective solid state light emitting devices is the LED chip emitting the G light (the second solid state light emitting device 221)>the LED chip emitting the R light (the first solid state light emitting device 211)>the LED chip emitting the B light (the third solid state light emitting device 231), the surface areas of the respective heat spreaders (the first heat spreader 313a, the second heat spreader 314a, and the third heat spreader 315a) may be changed to achieve the G light>the R light>the B light (the surface area of the second heat spreader 314a>the surface area of the first heat spreader 313a>the surface area of the third heat spreader 315a). Accordingly, cooling that matches each of the solid state light emitting devices may be performed.

Second Embodiment

Next, a second embodiment will be described. Although a case in which the present disclosure is applied to the rigid endoscope system using the rigid endoscope has been described in the aforementioned first embodiment, a case in which the present disclosure is applied to a flexible endoscope system using a flexible endoscope will be described in the second embodiment. Note that similar components to those in the endoscope system 1 according to the aforementioned first embodiment are labeled with the same reference signs, and description of the duplicate components is omitted.

Schematic Configuration of Endoscope System

Figure 8:
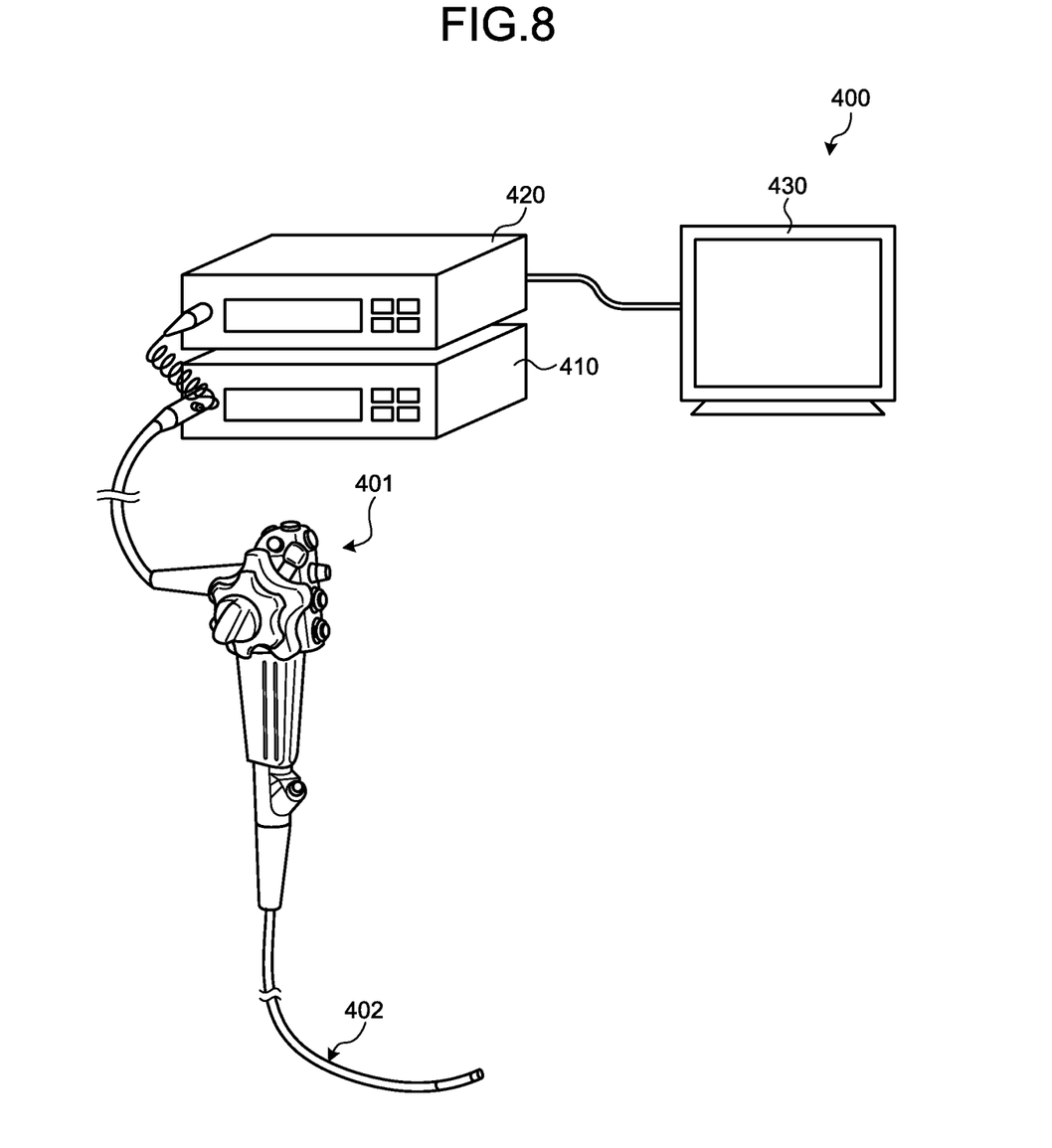
FIG. 8 illustrates a schematic configuration of an endoscope system according to a second embodiment.

FIG. 8 illustrates a schematic configuration of an endoscope system according to the second embodiment. An endoscope system 400 illustrated in FIG. 8 includes an endoscope 401 having an insertion unit thereof inserted into a subject to capture an in-vivo image of an observed region and generate an imaging signal, a light source device 410 having a similar configuration to that of the aforementioned light source device 3 and supplying white light or the like, a control device 420 performing predetermined image processing to the imaging signal that the endoscope 401 has acquired and comprehensively controlling operations of the entire endoscope system 400, and a display device 430 displaying the in-vivo image to which the control device 420 has performed the image processing.

The light source device 410 at least has a similar configuration to that of the aforementioned first embodiment.

According to the second embodiment described above, the flexible endoscope system 400 may also exert a similar effect to that of the aforementioned first embodiment.

Third Embodiment

Next, a third embodiment will be described. Although the endoscope system has been described in the aforementioned first and second embodiments, a case in which the present disclosure is applied to a surgical microscope system will be described in the third embodiment. Note that similar components to those in the endoscope system 1 according to the aforementioned first embodiment are labeled with the same reference signs, and description of the duplicate components is omitted.

Configuration of Surgical Microscope System

Figure 9:
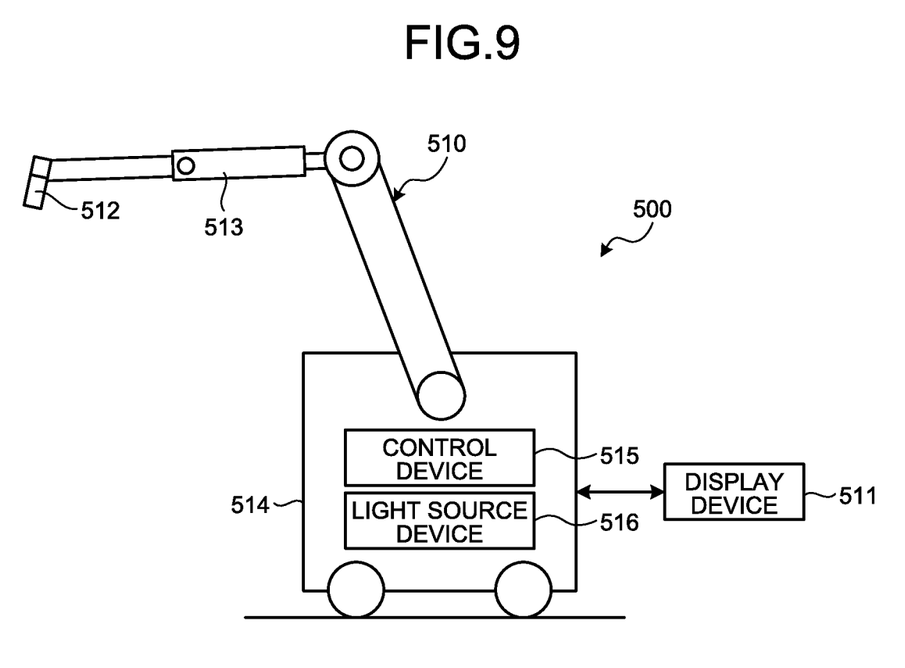
FIG. 9 illustrates a schematic configuration of a surgical microscope system according to a third embodiment.

FIG. 9 illustrates a schematic configuration of a surgical microscope system according to the third embodiment. A surgical microscope system 500 illustrated in FIG. 9 includes a microscope device 510 serving as a medical imaging device capturing and acquiring an image for observation of a subject and a display device 511 displaying the image that the microscope device 510 has captured. Note that the display device 511 and the microscope device 510 may be formed integrally.

The microscope device 510 includes a microscope unit 512 enlarging and capturing a micro part of the subject, a support unit 513 connected to a proximal end of the microscope unit 512 and including an arm turnably supporting the microscope unit 512, and a base unit 514 turnably holding a proximal end of the support unit 513 and movable on a floor surface. The base unit 514 includes a control device 515 controlling operations of the surgical microscope system 500 and a light source device 516 generating white light or the like to be emitted from the microscope device 510 to the subject. Note that the light source device 516 at least has a similar configuration to that of one of the aforementioned embodiment. Also, the base unit 514 may not be provided to be movable on the floor surface but may be secured to a ceiling, a wall surface, or the like to support the support unit 513.

The microscope unit 512 is formed in a cylindrical shape and has therein a lens unit and an imaging unit, for example. The side surface of the microscope unit 512 is provided with a switch receiving input of an instruction for operation of the microscope device 510. An aperture surface of a lower end portion of the microscope unit 512 is provided with cover glass protecting an inside of the microscope unit 512 (not illustrated).

In the surgical microscope system 500 configured as above, a user such as an operator moves the microscope unit 512, performs zooming, and switches illumination light while operating various switches in a state of holding the microscope unit 512. Note that the shape of the microscope unit 512 is preferably a shape causing the microscope unit 512 to extend in an elongated shape in an observation direction so that the user may hold the microscope unit 512 and easily change the viewing direction. For this reason, the shape of the microscope unit 512 may be other than the cylindrical shape and may be a polygonal columnar shape, for example.

According to the third embodiment described above, the surgical microscope system 500 may also exert a similar effect to that of the aforementioned first embodiment.

Other Embodiments

By appropriately combining the plurality of components disclosed in the aforementioned medical observation systems according to the first to third embodiments of the present disclosure, variations may be made. For example, some components may be deleted from all of the components described in the aforementioned medical observation systems according to the first to third embodiments of the present disclosure. Also, the components described in the aforementioned medical observation systems according to the first to third embodiments of the present disclosure may appropriately be combined.

Also, in the medical observation systems according to the first to third embodiments of the present disclosure, "unit" described above may be substituted with "means", "circuit", or the like. For example, the control unit may be substituted with the control means or the control circuit.

According to the present disclosure, an effect of enabling size reduction is exerted.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A light source device comprising:
a cooling device, the cooling device comprising:
a casing including an air intake port and an air exhaust port;
a single heat releaser including a plurality of fins arranged in a gas flow path from the air intake port to the air exhaust port;
a first heat diffuser arranged in the casing, connected to a first heat generation body generating heat at time of driving and the single heat releaser in a heat-transferable manner, and arranged at a position forming a part of the gas flow path passing through a space between the plurality of fins; and
a second heat diffuser arranged in the casing, connected to a second heat generation body generating heat at time of driving and the single heat releaser in a heat-transferable manner, and arranged at a position forming a part of the gas flow path passing through the space between the plurality of fins;
the first heat generation body; and
the second heat generation body,
wherein the first heat generation body is a first solid state light emitting device configured to emit light having a first wavelength band and is arranged on a first heat spreader,
the second heat generation body is a second solid state light emitting device configured to emit light having a second wavelength band and is arranged on a second heat spreader,
the casing includes:
a light emitter configured to supply light to an endoscope;
an optical member group configured to condense, collimate, and compound the light having the first wavelength band and the light having the second wavelength band to guide the light to the light emitter; and
an enclosure arranged to enclose the optical member group in the casing and configured to approximately seal the optical member group with use of the first heat diffuser and the second heat diffuser.

2. The light source device according to claim 1, further comprising:
a frame having a rectangular shape configured to house the plurality of fins in the single heat releaser and regulate arrangement of the plurality of fins,
wherein the first heat diffuser and the second heat diffuser are connected to the frame.

3. The light source device according to claim 2,
wherein the first heat diffuser and the second heat diffuser are arranged to be away from each other on the frame.

4. The light source device according to claim 3,
wherein the first heat diffuser and the second heat diffuser are arranged at positions opposed to the air intake port.

5. The light source device according to claim 2,
wherein the first heat diffuser includes the first heat spreader having a flat plate shape and arranged on a side surface of the frame perpendicular to a mounting surface on which the casing is mounted, and
the second heat diffuser includes the second heat spreader having a flat plate shape and arranged on the side surface of the frame perpendicular to the mounting surface on which the casing is mounted, which is same as the side surface on which the first heat spreader is arranged.

6. The light source device according to claim 5,
wherein the first heat diffuser further includes a first plurality of heat pipes each having one end thereof connected to the first heat spreader in a heat-transferable manner and each having another end thereof connected to the plurality of fins in a heat-transferable manner,
the second heat diffuser further includes a second plurality of heat pipes each having one end thereof connected to the second heat spreader in a heat-transferable manner and each having another end thereof connected to the plurality of fins in a heat-transferable manner, and
at least one of the first plurality of heat pipes and at least one of the second plurality of heat pipes are arranged on a side of the air intake port.

7. The light source device according to claim 1,
wherein the first heat diffuser includes the first heat spreader having a flat plate shape and arranged on a side surface of a frame perpendicular to a mounting surface on which the casing is mounted, and
the second heat diffuser includes the second heat spreader having a flat plate shape and arranged on the side surface of the frame perpendicular to the mounting surface on which the casing is mounted, which is same as the side surface on which the first heat spreader is arranged.

8. The light source device according to claim 7, wherein the first heat diffuser further includes a first plurality of heat pipes each having one end thereof connected to the first heat spreader in a heat-transferable manner and each having another end thereof connected to the plurality of fins in a heat-transferable manner, the second heat diffuser further includes a second plurality of heat pipes each having one end thereof connected to the second heat spreader in a heat-transferable manner and each having another end thereof connected to the plurality of fins in a heat-transferable manner, and at least one of the first plurality of heat pipes and at least one of the second plurality of heat pipes are arranged on a side of the air intake port.

9. The light source device according to claim 8, wherein the optical member group includes:
a first optical system arranged on an optical axis of the light having the first wavelength band emitted by the first solid state light emitting device and configured to condense and collimate the light having the first wavelength band;
a first lens frame configured to hold the first optical system and connected to the first heat diffuser;
a second optical system arranged on an optical axis of the light having the second wavelength band emitted by the second solid state light emitting device and configured to condense and collimate the light having the second wavelength band; and
a second lens frame configured to hold the second optical system and connected to the second heat diffuser.

10. The light source device according to claim 1, wherein the optical member group includes:
a first optical system arranged on an optical axis of the light having the first wavelength band emitted by the first solid state light emitting device and configured to condense and collimate the light having the first wavelength band;
a first lens frame configured to hold the first optical system and connected to the first heat diffuser;
a second optical system arranged on an optical axis of the light having the second wavelength band emitted by the second solid state light emitting device and configured to condense and collimate the light having the second wavelength band; and
a second lens frame configured to hold the second optical system and connected to the second heat diffuser.

11. A medical observation system comprising:
the light source device according to claim 10; and
an endoscope configured to emit light supplied from the light source device to a subject and receive light reflected on the subject to generate an image signal.

12. The light source device according to claim 1, wherein the second heat generation body has a larger heat generation amount than a heat generation amount of the first heat generation body, and
the second heat diffuser has a larger surface area than a surface area of the first heat diffuser.

13. A medical observation system comprising:
the light source device according to claim 12; and
an endoscope configured to emit light supplied from the light source device to a subject and receive light reflected on the subject to generate an image signal.

14. A medical observation system comprising:
the light source device according to claim 1; and
an endoscope configured to emit light supplied from the light source device to a subject and receive light reflected on the subject to generate an image signal.

15. A light source device comprising:
a cooling device;
the cooling device comprising:
a casing including an air intake port and an air exhaust port;
a single heat releaser including a plurality of fins arranged in a gas flow path from the air intake port to the air exhaust port;
a first heat diffuser arranged in the casing, connected to a first heat generation body generating heat at time of driving and the single heat releaser in a heat-transferable manner, and arranged at a position forming a part of the gas flow path passing through a space between the plurality of fins; and
a second heat diffuser arranged in the casing, connected to a second heat generation body generating heat at time of driving and the single heat releaser in a heat-transferable manner, and arranged at a position forming a part of the gas flow path passing through the space between the plurality of fins,
wherein the first heat diffuser includes a first heat spreader having a flat plate shape and arranged on a side surface of the frame perpendicular to a mounting surface on which the casing is mounted, and
the second heat diffuser includes a second heat spreader having a flat plate shape and arranged on the side surface of the frame perpendicular to the mounting surface on which the casing is mounted, which is same as the side surface on which the first heat spreader is arranged,
the first heat generation body; and
the second heat generation body,
wherein the first heat generation body is a first solid state light emitting device configured to emit light having a first wavelength band and is arranged on the first heat spreader,
the second heat generation body is a second solid state light emitting device configured to emit light having a second wavelength band and is arranged on the second heat spreader,
the casing includes:
a light emitter configured to supply light to an endoscope;
an optical member group configured to condense, collimate, and compound the light having the first wavelength band and the light having the second wavelength band to guide the light to the light emitter; and
an enclosure arranged to enclose the optical member group in the casing and configured to approximately seal the optical member group with use of the first heat diffuser and the second heat diffuser.

16. The light source device according to claim 15, wherein the optical member group includes:
a first optical system arranged on an optical axis of the light having the first wavelength band emitted by the first solid state light emitting device and configured to condense and collimate the light having the first wavelength band;
a first lens frame configured to hold the first optical system and connected to the first heat diffuser;
a second optical system arranged on an optical axis of the light having the second wavelength band emitted by the second solid state light emitting device and configured to condense and collimate the light having the second wavelength band; and a second lens frame configured to hold the second optical system and connected to the second heat diffuser.

17. A medical observation system comprising:

the light source device according to claim 16; and an endoscope configured to emit light supplied from the light source device to a subject and receive light reflected on the subject to generate an image signal.

18. The light source device according to claim 15, wherein the second heat generation body has a larger heat generation amount than a heat generation amount of the first heat generation body, and the second heat diffuser has a larger surface area than a surface area of the first heat diffuser.

19. A medical observation system comprising:

the light source device according to claim 18; and an endoscope configured to emit light supplied from the light source device to a subject and receive light reflected on the subject to generate an image signal.

20. A medical observation system comprising:

the light source device according to claim 15; and an endoscope configured to emit light supplied from the light source device to a subject and receive light reflected on the subject to generate an image signal.

* * * * *